(12) United States Patent
Simonov et al.

(10) Patent No.: US 9,622,852 B2
(45) Date of Patent: Apr. 18, 2017

(54) INTRAOCULAR LENSES FOR VARIABLE FOCUS

(75) Inventors: Aleksey Nikolaevich Simonov, The Hague (NL); Michiel Christiaan Rombach, Breda (NL)

(73) Assignee: Akkolens International B.V., Breda (NL)

(*) Notice: Subject to any disclaimer, the term of this patent is extended or adjusted under 35 U.S.C. 154(b) by 469 days.

(21) Appl. No.: 13/505,198

(22) PCT Filed: Oct. 29, 2010

(86) PCT No.: PCT/NL2010/050725
§ 371 (c)(1),
(2), (4) Date: Aug. 22, 2012

(87) PCT Pub. No.: WO2011/053143
PCT Pub. Date: May 5, 2011

(65) Prior Publication Data
US 2012/0323321 A1   Dec. 20, 2012

(30) Foreign Application Priority Data

Oct. 30, 2009  (NL) .................................... 2003731

(51) Int. Cl.
*A61F 2/16*   (2006.01)
*G02C 7/08*   (2006.01)

(52) U.S. Cl.
CPC .......... *A61F 2/1613* (2013.01); *A61F 2/1629* (2013.01); *A61F 2/1648* (2013.01); *G02C 7/081* (2013.01)

(58) Field of Classification Search
CPC ..... A61F 2/1629; A61F 2/1648; A61F 2/1632

USPC ........................................................ 623/6.34
See application file for complete search history.

(56) References Cited

U.S. PATENT DOCUMENTS

| 3,305,294 A | 2/1967 | Alvarez |
| 5,275,623 A | 1/1994 | Sarfarazi |
| 5,674,282 A | 10/1997 | Cumming |
| 6,197,059 B1 | 3/2001 | Cumming |
| 7,871,437 B2 | 1/2011 | Hermans et al. |
| 8,182,531 B2 | 5/2012 | Hermans et al. |

(Continued)

FOREIGN PATENT DOCUMENTS

| AU | 2004202852 A1 | 7/2004 |
| WO | 9615734 A2 | 5/1996 |

(Continued)

OTHER PUBLICATIONS

Bernet et al., Adjustable refractive power from diffractive moire elements, Applied Optics, Jul. 20, 2008, pp. 3722-3730, vol. 47, No. 21.

(Continued)

*Primary Examiner* — David Isabella
*Assistant Examiner* — Christine Nelson
(74) *Attorney, Agent, or Firm* — The Webb Law Firm

(57) ABSTRACT

A novel lens for variable focus has two optical elements which simultaneously move in a lateral and an axial direction. The lens also includes variable corrective optics to correct for undesired variable optical aberrations. The lens can be used as an accommodating lens for implantation in the capsular bag. The lens can be driven by either the surfaces of the capsular bag as well as the rim of the capsular bag.

5 Claims, 5 Drawing Sheets

(56) References Cited

U.S. PATENT DOCUMENTS

| | | |
|---|---|---|
| 2002/0179040 A1 | 12/2002 | Dalla Betta |
| 2005/0060032 A1 | 3/2005 | Magnante et al. |
| 2006/0259139 A1 | 11/2006 | Zadno-Azizi et al. |
| 2008/0046076 A1 | 2/2008 | Rombach |
| 2008/0215146 A1 | 9/2008 | Rombach |
| 2009/0018652 A1 | 1/2009 | Hermans et al. |
| 2009/0062912 A1 | 3/2009 | Rombach |
| 2009/0088841 A1* | 4/2009 | Hong et al. ............ 623/6.37 |
| 2009/0204211 A1* | 8/2009 | Angelopoulos et al. .... 623/6.37 |
| 2010/0094413 A1 | 4/2010 | Rombach et al. |
| 2010/0134869 A1 | 6/2010 | Bernet et al. |
| 2010/0280609 A1 | 11/2010 | Simonov et al. |
| 2011/0112638 A1 | 5/2011 | Hermans et al. |
| 2012/0069320 A1 | 3/2012 | Simonov et al. |
| 2012/0232650 A1 | 9/2012 | Hermans et al. |

FOREIGN PATENT DOCUMENTS

| | | |
|---|---|---|
| WO | 02071983 A1 | 9/2002 |
| WO | 2005084587 A2 | 9/2005 |
| WO | 2006118452 A1 | 11/2006 |
| WO | 2008071760 A2 | 6/2008 |
| WO | 2008077795 A2 | 7/2008 |
| WO | 2009012789 A1 | 1/2009 |
| WO | 2009051477 A2 | 4/2009 |
| WO | 2010080030 A2 | 7/2010 |
| WO | 2011102719 A1 | 8/2011 |

OTHER PUBLICATIONS

Masket, Accommodating IOLS: Emerging Concepts and Designs, Cataract & Refractive Surgery Today, Jul. 2004, pp. 32-37.

* cited by examiner

INTRAOCULAR LENSES FOR VARIABLE FOCUS

BACKGROUND OF THE INVENTION

1) Field of the Invention

The present document describes lenses for variable focus which provide variable focus, including technical lenses for variable focus for, for example, cameras and medical lenses for variable focus, for, for example, outside the eye, spectacles, or for inside the eye, as intraocular lenses, henceforth: "IOLs", in particular accommodating intraocular lenses, henceforth: "AIOLs". The lenses for variable focus disclosed in the present document can be optical components of said cameras, of spectacles and of intraocular lenses with application of said lenses not restricted thereto. Optical and mechanical principles of such lenses for variable focus are similar for the technical and the medical applications of such lenses. For illustration and explanation the IOLs and AIOLs will be used henceforth to set forth the optical and mechanical principles of these lenses for variable focus.

2) Discussion of the Prior Art

IOLs replace the natural lens of the eye when the natural lens is removed during cataract surgery, as an aphakic lens, or used in the eye as an addition to the natural lens, as a phakic lens. Intraocular lenses are generally monofocal and offer sharp vision at one distance only. AIOLs provide sharp vision over a range of distances, from, for example, reading distance up to infinity by variable focus and AIOLs are generally driven by contraction and relaxation of muscles of the human eye which also drives the natural process of accommodation. Principles for AIOLs include lateral and axial movement of optical elements, as set forth in, for example, S. Masket, *Cataract and refractive surgery today*, July 2004, pp. 34-37. Axial movement, in the context of the present document, means movement along the optical axis of the lens.

SUMMARY OF THE INVENTION

The present document discloses lenses for variable focus with at least two optical elements comprising surfaces for focusing by lateral movement, meaning movement substantially perpendicular to the optical axis, of the optical elements in combination with surfaces for focusing by axial movement, meaning movement along the optical axis, of the elements in which variable focus is achieved by simultaneous axial movement and lateral movement of at least one of the optical elements. The combination of said variable foci exceeds the degree of variable focus of only laterally or only axially moving optical elements.

IOLs including lenses for variable focus adapted to provide a variable degree of focus disclosed in the present document comprise at least two optical elements. Each optical element comprises at least one surface for optical function, a surface with a shape adapted to perform an optical function, for example, providing a cubic wavefront as by a cubic surface, providing focusing of light as by a spherical lens or providing correcting of at least one aberration other than focus as by specialized surfaces designed for such purpose. (Note that, in the context of this document, focus is regarded an optical aberration.)

The optical elements have at least one surface for focusing by lateral movement which surfaces are adapted to provide variable focus of which the degree of focus depends on the relative lateral position of the optical elements. The optical elements also have at least one surface for focusing by axial movement which surfaces are adapted to provide variable focus of which the degree of focus depends on the relative axial position of the optical elements.

The variable focus of the lens for variable focus is a combination of variable focus provided by at least one surface for focusing by lateral movement and variable focus provided by at least one surface for focusing by axial movement.

According to a preferred embodiment the lenses generally have at least one additional surface for variable correction of variable aberrations other than variable focus. Such additional surfaces can correct for, for example, variable aberrations caused by lateral movement of components of the lens relative to the optical axis of, for example, the cornea. The principles of such variable correction are disclosed in WO2008,071,760. So, the lens comprises at least one additional surface for variable correction of variable aberrations other than variable focus to provide variable correction of at least one variable aberration of which the degree of correction depends on the relative position of the optical element. Such surfaces can be designed to correct by lateral movement or by rotational movement.

The lens can, but not necessarily has to, include at least one additional surface for fixed correction of fixed aberrations other than fixed focus. Such additional surfaces can correct for, for example, a fixed astigmatism of the cornea of the eye, a standard correction provided by modern IOLs. The lens can also, but not necessarily has to, include at least one additional surface for fixed correction fixed focus. Such additional surface can correct for, for example, the fixed refractive error of the eye due to removal of the natural lens. This is the standard correction and main function provided by all aphakic IOLs.

DETAILED DESCRIPTION OF THE PREFERRED EMBODIMENTS

Figure 1:
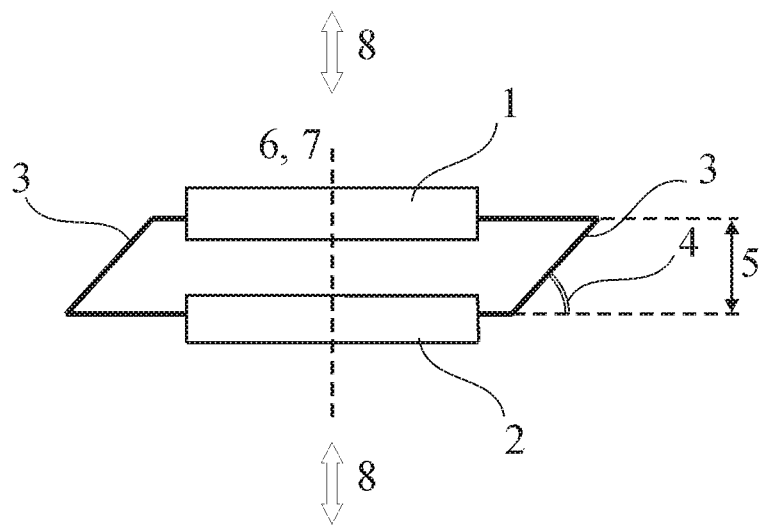
FIG. 1 is a diagram of a first embodiment of an AIOL, at rest, at low diopter power.

As stated above, a first embodiment uses two optical elements with an optical surface each. Another embodiment of the present invention provides an intraocular lens having a variable focus and comprising at least two optical elements with each of these elements comprising at least one surface for optical function which surfaces include at least two surfaces provided on different optical elements for focusing by lateral movement of the optical elements which surfaces are adapted to provide variable focus of which the degree of focus depends on the relative lateral position of the optical elements and at least two surfaces provided on different optical elements for focusing by axial movement of the optical elements which surface is adapted to provide variable focus of which the degree of focus depends on the relative axial position of the optical elements, wherein the lens comprises a structure connected to the optical elements allowing and defining a simultaneous mutual lateral and axial movement of the optical elements and that the variable focus of the lens is a combination of variable focus provided by at least one surface for focusing by lateral movement and variable focus provided by at least one surface for focusing by axial movement.

Herein the optical elements may each comprise two optical elements, each of which comprising two optical surfaces, each element having both a surface for focussing by lateral movement and one for focussing by axial movement. It is however also possible to make use of three optical elements, one of which comprising two optical surfaces and the two others each comprising one optical surface. Herein the optical element comprising two optical surfaces must comprise a surface for focussing by lateral movement and one by axial movement, while the two remaining optical elements comprise a surface for focussing by lateral movement or a surface for focussing by axial movement. Further it will be clear that the optical element comprising two optical surfaces is movable relative to the other two optical elements to obtain the effect of the invention.

Surfaces for focusing by lateral movement include surfaces adapted to provide variable focus by translation along a single axis perpendicular to the optical axis relative to at least one other such surface, such surfaces being cubic surfaces, as described in, for example, U.S. Pat. No. 3,305, 294. Such lenses for variable focus comprising cubic surfaces are included in other AIOLs as well, as disclosed in, for example, US2008,046,076, WO2009,051,477, US2008, 215,146, US2009,062,912, WO2006,118,452 and WO2008, 071,760.

Surfaces for focusing by lateral movement also include surfaces adapted to provide variable focus by rotation in a plane perpendicular to the optical axis of at least one such surface relatively to at least one other such surface. For example, rotating surfaces adapted to provide variable focal power are set forth in, for example, WO2005,084,587 and fan-like rotating surfaces in WO2008,077,795 can likely be adapted for lenses described in the present document. However, screw-type surfaces, for example, parabolic screw surfaces, or derivations thereof, as described in WO2010, 080,030, for largely technical use, and their intraocular use forms the subject of the document NL2,004,255, Chiral multifocal ophthalmic lens, both documents relate to largely refractive smooth surfaces, are well suited for the purpose of providing variable focus by rotation of at least two optical elements comprising at least one such screw type optical surface each. Rotation of optical elements for variable focus using multiple screw-type diffractive surfaces (also: moiré diffractive optical elements, abbr.: moiré DOE) is described in *Adjustable refractive power from diffractive moiré elements*, S. Bernet and M. Ritsch-Marte, Appl. Opt. 47, 3722-3730, 2008 and in WO2009,012,789. Both smooth refractive surfaces as well as diffractive surfaces can be adapted to provide optical functions for IOLs and AIOLs.

Surfaces for focusing by axial movement include generally traditional symmetrical spherical surfaces on two optical elements in a basic telescopic arrangement, for example a Galilean or a Newtonian telescopic optical arrangement. At least one of the optical element moves along the optical axis, an axial movement, as in, for example, AIOLs described in U.S. Pat. No. 6,197,059 and U.S. Pat. No. 5,674,282, or in U.S. Pat. No. 5,275,623. Such movement provides variable focus of which the degree of focus depends on the relative position of the optical elements, as in a telescope.

Note that such lenses for variable focus can, in theory, be composed of two optical elements and only two surfaces for optical function, one surface per optical element, for example, one element with one progressive surface for focusing by lateral movement and another element with only one spherical surface for focusing by axial movement. So, a simple embodiment of lenses disclosed in the present document is a lens comprising at least one lens for variable focus comprising at least two optical elements with each of these elements comprising at least one surface for optical function. The surfaces include one surface provided on one optical element for focusing by lateral movement which surface is adapted to provide variable focus of which the degree of focus depends on the lateral position of the optical element, and one surface provided on any other optical element for focusing by axial movement which surface is adapted to provide variable focus of which the degree of focus depends on the axial position of the optical element. The lens also comprises at least one connecting component connected to the optical elements allowing and defining a simultaneous mutual lateral and axial movement of the optical elements and that the variable focus of the lens is a combination of variable focus provided by the surface for focusing by lateral movement and variable focus provided by the surface for focusing by axial movement. However, in practice, most applications, including intraocular applications, require optical quality which can be provided only by a design including more than two surfaces for optical function, for example, two progressive surfaces, for example cubic surfaces, for focusing by lateral movement in combination with two symmetrical surface, for example spherical surfaces in a telescopic arrangement, for focusing by axial movement, in combination with at least one additional surface for variable correction of variable aberrations other than focus and likely at least one additional surface for fixed correction of fixed aberrations other than fixed focus, and likely at least one additional surface for fixed correction fixed focus. These are complex optical arrangements. However, multiple surfaces of any kind can be combined in composite surfaces which composite surfaces are adapted to provide at least two optical functions simultaneously.

Figure 5:
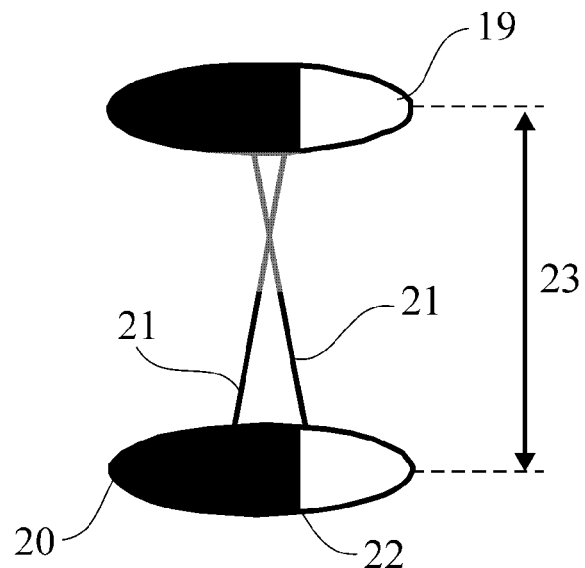
FIG. 5 is a perspective diagram of an AIOL wherein the movement of the optical elements is a combination of movements along the optical axis, as in a telescopic arrangement, and rotation of the optical elements, with the AIOL in rested state, of relatively low diopter power.
Figure 6:
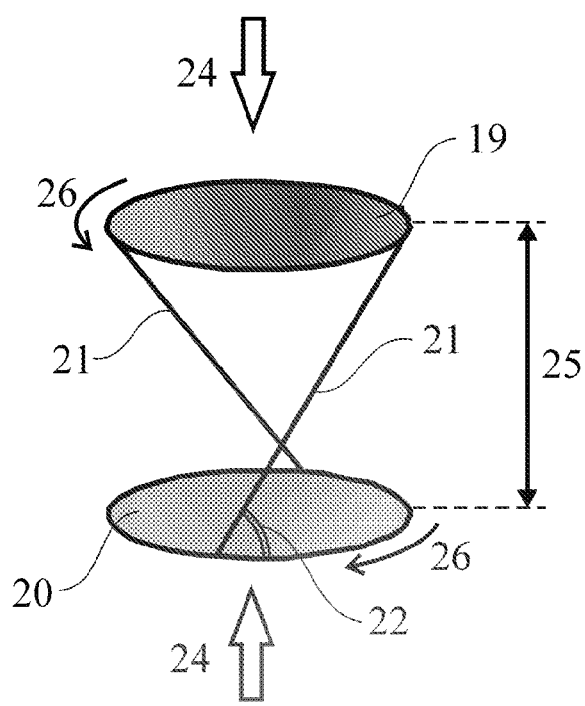
FIG. 6 is a perspective diagram of an AIOL wherein the movement of the optical elements is a combination of movement along the optical axis, as in a telescopic arrangement, and rotation of the optical elements, with the AIOL in accommodated state, of relatively high diopter power.

The accommodative power of presently commercially available AIOLs of telescopic design, as, for example, described in AU 2004,202,852, US2002,179,040 and US2006,259,139 and numerous variations on Galilean or Newtonian telescope designs can be significantly increased by addition of, for example, said screw typed surfaces and the required addition of connecting components, for example, cross-type connecting components, which allows for simultaneous movement along the optical axis and rotation of at least one optical element (see also FIG. 5-6).

To achieve simultaneous mutual movement of optical elements along, alternatively, in the direction of, more than one axis the optical elements are fitted in at least one connecting component for simultaneous movement which component is adapted to connect the optical elements and to provide simultaneous movement of the optical elements in at least one lateral direction and in at least one axial direction (with axial directions being positive or negative. The lens and connecting element can also include supporting components such as haptics, for example flanges, hooks or loops, to facilitate positioning of the IOL in the eye, for example in the capsular bag, in the sulcus or in the iris of the eye, which haptic design can differ between different positioning and between different types of IOLs and AIOLs.

In summary, at emmetropia the eye is focused at a distance, ciliary muscle is relaxed, zonulae are tense, accommodative power is minimal, capsular bag is stretched and exerts, by means of its anterior and posterior surfaces, a compressing force parallel to the optical axis on optical elements resulting in translation and shift of elements, decreasing distance between elements, and shifts of elements to a position of maximum overlap, and at accommodation the eye is focused at nearby, ciliary muscle is contracted, zonulae are relaxed, accommodative power is maximal, capsular bag is contracted by its inherent elasticity, compressing force parallel to the optical axis is minimal translating and shifting the elements due to resilience of the lens, increasing the distance between the elements and minimizing overlap of the elements.

So, the resilience of the connecting components allows the AIOL to expand in absence of forces. At least one of the hinges, the elastic fraction of the connecting component, should have a resilient action to bring the optical elements to a position with the maximum distance between the optical elements. Additionally, the hinges should facilitate the reversible reduction of the distance between the optical elements under compressing force exerted, for example, by the capsular bag. In practice, driving forces should exceed the resilient action of hinges and, in turn, the resilient action of hinges should exceed elasticity of the capsular bag. So, the lens is compressed by muscle forces and expanded by lens resilience. This moves the optical elements, for example, in accordance with FIGS. 1 and 2, to a position with minimum overlap and maximum distance in an accommodated eye and maximum overlap and minimum distance in an emmetropic eye. Note that, if required, the accommodative lens can be adapted such that a position with the minimum overlap and the maximum distance corresponds to emmetropia, and vice-versa for correspondence to accommodation.

As in FIG. 1-2 and FIG. 3-4, the optical elements can be connected by at least one swivable connecting component to simultaneously provide at least one lateral translation movement and at least one axial movement to at least one optical element. For example, the component can convert intraocular movements, for example, contraction of the capsular bag, into a combined axial and lateral movement, in this case translation, of the optical elements. For example, the connecting component comprises a first connecting element of which one end is swivably connected to a first side of the first optical element and a second end is swivably connected to the first side of the second optical element and a second connecting element of which one end is swivably connected to a second side opposite the first side of the first optical element and a second end is swivably connected to the second side opposite the first side of the second optical element, wherein both connecting elements and both optical elements are together adapted to form the structure of a variable parallelogram.

The swivable connecting component can be adapted such that the optical elements are driven by, first, forces parallel to the optical axis exerted by, for example, at least one, inner surface of the capsular bag onto, at least one, optical element, second, forces perpendicular to the optical axis exerted by, for example, the rim of the capsular bag onto, at least one, connecting component and, third, combinations of said forces. It is required that the combines resilience of connecting components does not exceed the compression force of the muscle as exerted by the capsular bag as to allow compression of the lens, but does exceed the force of the capsular bag itself as to allow the lens to return to the relaxed state once the muscle force subsides.

Alternatively, as in FIG. 5-6, the optical elements can be connected by at least one cross-type connecting component which simultaneously provides at least one lateral rotation movement and at least axial movement. (Cross-type refers to crossing of the connecting components at side-view of the lens, as illustrated in FIG. 5 and FIG. 6.) The AIOL, as in FIG. 5-6, has two optical elements carrying, firstly, a lens for variable focus with two optical elements with at least one spherical surface each, the anterior element with at least one convex surface and the posterior element with at least one concave surface, as in the arrangement of a traditional Galilean telescope. This arrangement is combined with, secondly, a second variable focus arrangement comprised of two cubic surfaces, one such surface on each optical element. The variable focus of the lens is achieved by the combination of said telescope and the additional variable focus arrangements resulting in a combination of variable foci. In practice, such embodiment will require at least two additional surfaces for variable correction of variable aberrations, as described in WO2008,071,760 and likely also require at least one additional surface for fixed correction of fixed aberrations other than fixed focus and at least one additional surface for fixed correction fixed focus. All these surfaces can be combined with any other surfaces in composite surfaces. The cross-type connecting component converting the intraocular movements, for example, contraction of the capsular bag, into a combined axial and lateral movement, in this case rotation, of the optical elements. One end of each cross-type connecting component is connected to the rim of the first optical element and the other end of each connecting component is connected to the rim of the second optical element. The optical power of the lens changes as a result of mutual rotation movement of the optical elements in combination with axial movement. A configuration with two connecting components is shown here for ease of reference, but for mechanical stability of the construction three or more connecting components is preferred.

So, such lens comprises a combination of a lens for variable focus comprising a telescope arrangement, Galilean or Newtonian or other alternative design, and a lens for variable focus comprising at least one surface for focusing by lateral movement which lateral movement can be a translation along a single axis perpendicular to the optical axis or a rotation in a single plane perpendicular to the optical axis or a combination of rotation and translation.

Additional Comments:

Stoppers can be added to limit movement of the optical elements in selected directions, for example to prevent movement beyond position of the optical elements which position represents an emmetrope eye; The accommodative lens can be assembled of optical/mechanical elements made of different material, for example, optical elements which differ from connecting elements; Optics can be refractive or diffractive, or, for non-intraocular use, reflective; Hinges can have reduced thickness at the connection with optical elements to adjust the resilience/elasticity; Width of the connecting elements is generally smaller than the width of the optical elements, in the same direction; Additional extension of optical surfaces, beyond the connection with the connecting elements, prevents tilt of the accommodative lens due to inherent asymmetry in force distribution; Additional haptics, for example T-shaped haptics, added to the connecting components improve efficiency of transfer of movement of the rim of the capsular bag to the optical elements; Ratio of translation/shift can be affected by design of the angle, depending on design, the orbital angle of the connecting component and the optical element or the variable angle of the connecting components versus the plane of the optical elements, see also FIGS. 1-2 and 5-6; The IOLs described in the present document can be adjustable IOLs for the phakic eye, AIOLs for the aphakic eye, with the AIOLs positioned in the capsular bag, in the sulcus of the eye in front of the capsular bag or in the iris of the eye.

FIGURES

FIG. 1, diagram of a first embodiment of an AIOL, at rest, at low diopter power, (FIG. 1 in combination with FIG. 2), with an anterior optical element, 1, with at least one surface for focusing, a posterior optical element, 2, also with at least one surface for focusing, a swivable connecting component, 3, the variable angle of the connecting components versus the plane of the optical elements, 4, the variable distance between the optical elements, 5, the optical axis of the first element, 6, the optical axis of the second element, 7, with the lens at rest in overlap, and the direction of the driving force, 8, in this example, along the optical axis, in axial direction.

Figure 2:
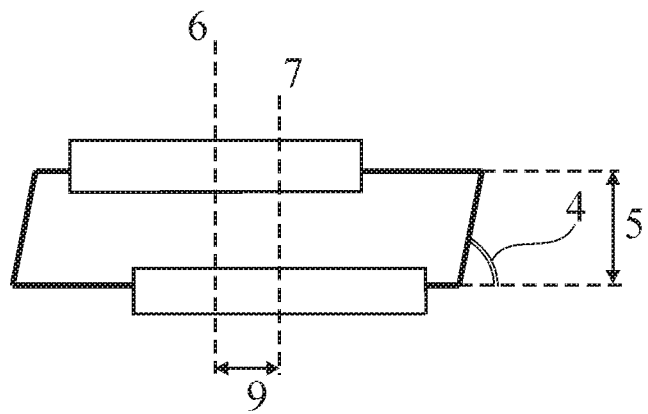
FIG. 2 is a diagram of a first embodiment of an AIOL, at accommodation, at high diopter power.

FIG. 2, diagram of a first embodiment of an AIOL, at accommodation, at high diopter power, (FIG. 2 in combination with FIG. 1; for 1-8, refer to FIG. 1), with separated optical axes by a distance, 9, the separation due to lateral movement of the optical elements.

Figure 3:
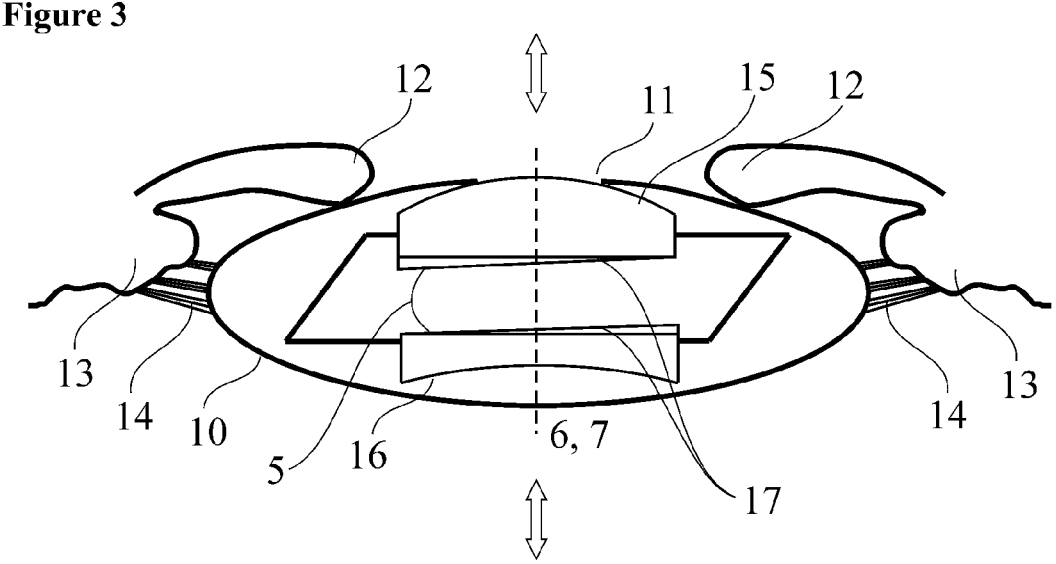
FIG. 3 is a diagram of an AIOL, at rest, at low diopter power, in the capsular bag.

FIG. 3, diagram of an AIOL, at rest, at low diopter power, in the capsular bag, (FIG. 3 in combination with FIG. 4; for 1-9 refer to FIG. 1-2), with the capsular bag, 10, the capsulorrhexis, 11, the iris, 12, the ciliary muscle, 13, the zonulae, 14, surfaces for focusing by axial movement, comprising a telescope arrangement including a positive spherical lens, 15, and a negative lens, 16, and surfaces for focusing by lateral movement, an arrangement of cubic surfaces, 17. The combination of the telescope arrangement and arrangement of cubic surfaces provide the combination of foci of the AIOL. The distance, 5, between the optical elements is small.

Figure 4:
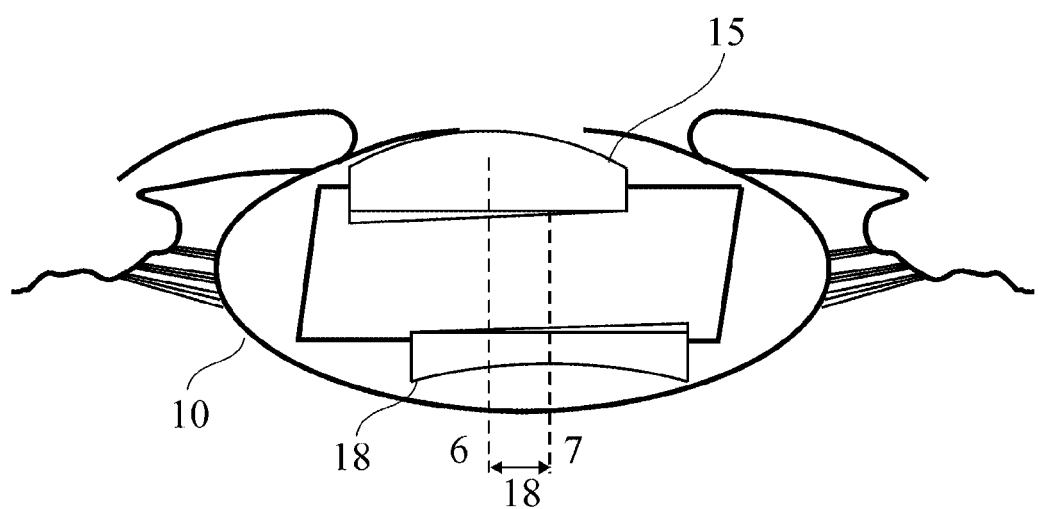
FIG. 4 is a diagram of a preferred embodiment of an AIOL, at accommodation, at high diopter power, in the capsular bag.

FIG. 4, diagram of a preferred embodiment of an AIOL, at accommodation, at high diopter power, in the capsular bag, (FIG. 4 in combination with FIG. 3; 1-17, refer to FIGS. 1-3), with distance between the optical axi, 18, increased compared to the distance, 5, in FIG. 3, which is due to lateral movement of the optical elements.

Figure 3A:
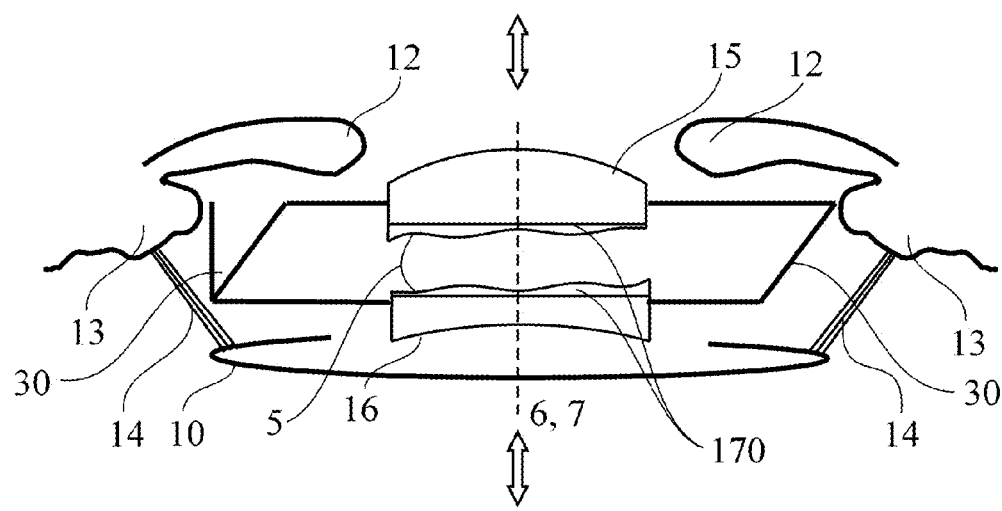

FIG. 3A, diagram of an AIOL, at rest, at low diopter power, in the sulcus of the eye, (FIG. 3A in combination with FIG. 4A; for 1-9 refer to FIGS. 1-2), with the capsular bag, 10, the iris, 12, the ciliary muscle, 13, the zonulae, 14, surfaces for focusing by axial movement, comprising a telescope arrangement including a positive spherical lens, 15, and a negative lens, 16, and composite surfaces, 170, that combine surfaces for focusing by lateral movement and surfaces for variable correction of variable aberrations other than defocus, a composite arrangement of surfaces. The combination of the telescope and composite arrangements provides variable focusing and correction of variable aberrations other than defocus. The distance, 5, between the optical elements is small. The connecting and supporting component, 30, is adapted for sulcus placement of the AIOL.

Figure 4A:
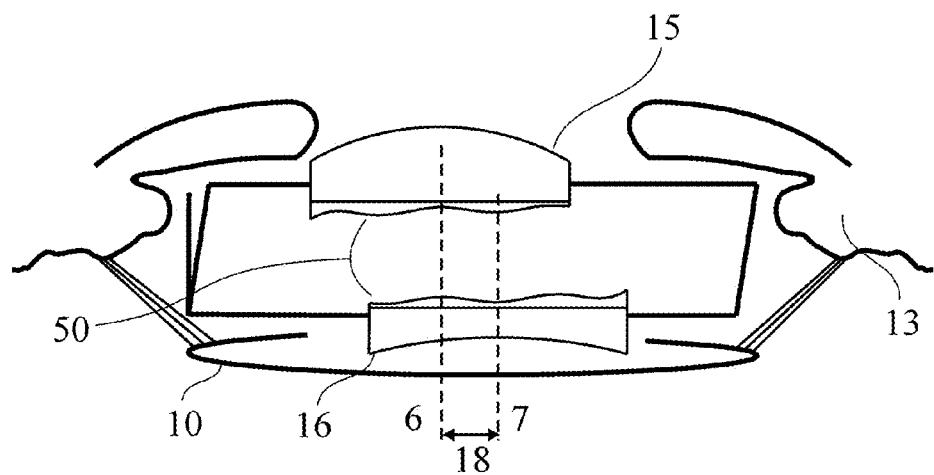

FIG. 4A, diagram of a preferred embodiment of an AIOL, at accommodation, at high diopter power, in the sulcus of the eye, (for 6, 7, 10, 13, 15, 16 refer to FIG. 3A), with the increased distance, 18, between the optical axes, 6 and 7, and the increased distance 50 between the optical elements. The distances increase due to lateral and axial movements of the optical elements in accommodation.

FIG. 5, a perspective diagram of an AIOL wherein the movement of the optical elements is a combination of movements along the optical axis, as in a telescopic arrangement, and rotation of the optical elements, with the AIOL in rested state, of relatively low diopter power (FIG. 5 in combination with FIG. 6), with an anterior optical element, 19, comprising a screw-type surface, a spherical surface and several types of additional surfaces for correction, and a posterior optical element, 20, also with a screw-type surface, a spherical surface and several types of additional surfaces for correction, cross-type connecting components, 21, and, in this position, relative large orbital angle of the connecting component and the optical element, 22, and the optical elements separated by a distance, 23.

FIG. 6 a perspective diagram of an AIOL wherein the movement of the optical elements is a combination of movement along the optical axis, as in a telescopic arrangement, and rotation of the optical elements, with the AIOL in accommodated state, of relatively high diopter power (FIG. 6 in combination with FIG. 5, for 19-23 refer to FIG. 5), with compression force, 24, for example a force exerted by the inner faces of the capsular bag compressing the intraocular lens, which force decreases the distance, 25, between the optical elements while simultaneously rotating, 26, the optical elements relatively to each other in a plane perpendicular to the optical axis.

Figure 5A:
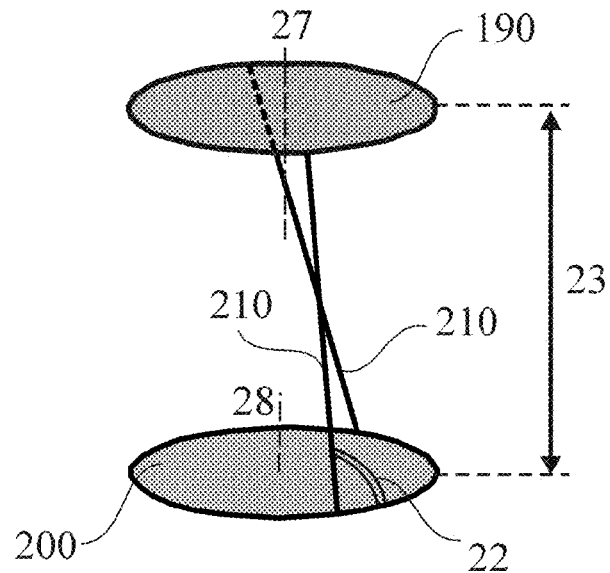

FIG. 5A, a perspective diagram of an AIOL wherein the movement of the optical elements is a combination of movements along the optical axis, rotation and translation. The AIOL is at rest with low diopter power (FIG. 5 in combination with FIG. 6), with an anterior optical element, 190, comprising a screw-type surface, a spherical surface and several types of additional surfaces for correction and focusing by translational movement, and a posterior optical element, 200, also with a screw-type surface, a spherical surface and several types of additional surfaces for correction and focusing by translational movement, cross-type connecting components, 210, and, in this position, providing simultaneous axial, rotational and translational movements of the optical elements. The elements are separated by an axial distance, 23, and orbital angle, 22, is large and their optical axes, 27 and 28, are aligned.

Figure 6A:
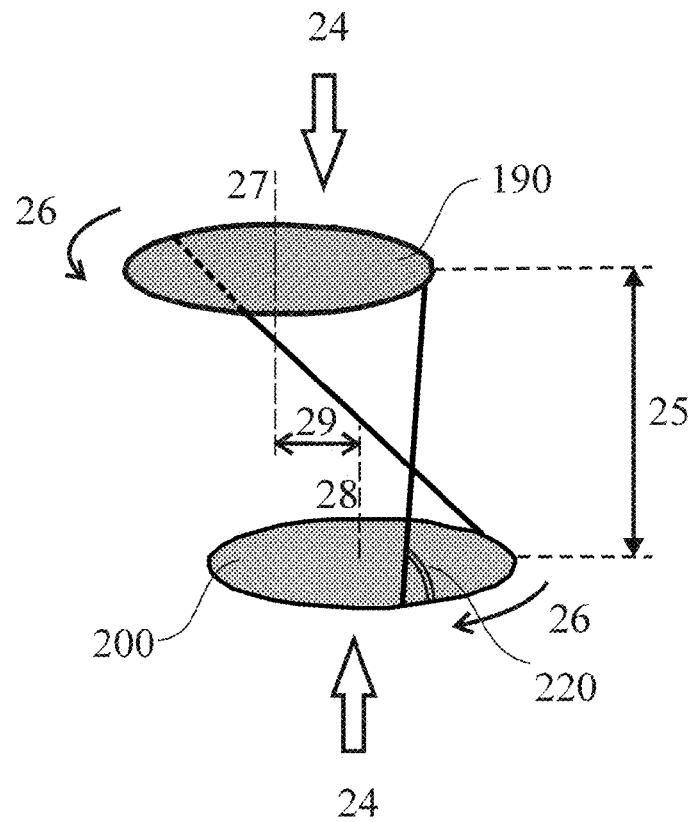

FIG. 6A, wherein the movement of the optical elements is a combination of movements along the optical axis, rotation and translation. The AIOL in accommodation, of relatively high diopter power (FIG. 6 in combination with FIG. 5, for 27, 28, 190, 200 refer to FIG. 5), with compression force, 24, for example a force exerted by the inner faces of the capsular bag compressing the intraocular lens, which force decreases the distance, 25, between the optical elements while simultaneously rotating, 26, the optical elements relatively to each other and displacing them, 29, in a plane perpendicular to the optical axes 27 and 28.

EXAMPLE

This example refers to a lens as illustrated in FIG. 1-2. Assuming that $h_0$ is the distance, 5, between the optical elements and $\alpha_0$ is the angle, 4, at emmetropia (FIG. 1) and $h_1$ is the distance, 5, and $\alpha_1$ the angle, 4, at accommodation (FIG. 2) it can be found that:

$$h_0/\sin\alpha_0 = h_1/\sin\alpha_1, \qquad (1)$$

$$\Delta d = \frac{h_0}{\sin\alpha_0}(\cos\alpha_1 - \cos\alpha_0), \qquad (2)$$

$$\Delta h = \frac{h_0}{\sin\alpha_0}(\sin\alpha_0 - \sin\alpha_1), \qquad (3)$$

with $\Delta h = h_0 - h_1$ representing the axial movement between the optical elements. Due to the lateral movement $\Delta d$ the overlap between the refractive elements, representing diameter of optical aperture, is reduced by $2\Delta d$ in the direction of the shift, in this example a change in angle of $\alpha_1 \cong 21°$ results in a $\Delta d = 0.6$ mm and the corresponding change in distance, 5, is $\Delta h \cong 0.7$ mm. In these estimates it was taken that (at rest): $\alpha_0 = 0°$, $h_0 = 1.2$ mm.

Assuming that a force F on the connecting elements, 3. For an element of $\theta = \theta(l)$ the equation from Landau and Lifshitz (Parag. 19, *Theory of Elasticity*, Pergamon, N.Y., 1970) is adapted:

$$IE\frac{d^2\theta(l)}{dl^2} + F\sin\theta = 0, \qquad (4)$$

with E the Young's modulus of the material, in this case an hydrophobic acrylic polymer, and I the momentum of inertia in cross section relative to the $\xi$-axis:

$$I \equiv I_\xi = \frac{b^3 a}{12}, \qquad (5)$$

with a and b the lateral dimensions of the connective elements. So, the local bending momentum at l becomes:

$$M = EI\frac{d\theta}{dl}. \qquad (6)$$

with boundary conditions for Eq. (4):

$$\theta = \theta_0 = \frac{\pi}{2} - \alpha_0 \text{ at } l = l_0 \qquad (7)$$

$$\theta = \theta_1 \text{ at } l = s/2$$

$$M = EI\frac{d\theta}{dl} = -x(\theta_1)F,$$

with $\theta_1$ the angle in the centre of the connecting element, at point O', and s the length of the connecting element. Eq. (4) and Eqs. (7) gives, within the range $\theta_0 \leq \theta \leq \theta_1$ and $0 \leq l \leq s/2$:

$$l(\theta) = \sqrt{\frac{EI}{2}} \int_{\theta_0}^{\theta} \frac{d\vartheta}{\sqrt{C_1 + F\cos\vartheta}}, \qquad (8a)$$

$$x(\theta) = \sqrt{\frac{EI}{2}} \int_{\theta_0}^{\theta} \frac{\sin\vartheta d\vartheta}{\sqrt{C_1 + F\cos\vartheta}}, \qquad (8b)$$

$$y(\theta) = \sqrt{\frac{EI}{2}} \int_{\theta_0}^{\theta} \frac{\cos\vartheta d\vartheta}{\sqrt{C_1 + F\cos\vartheta}}, \qquad (8c)$$

where $C_1 = \frac{EI}{2}\left(\frac{sF\sin\theta_1}{2EI}\right)^2 - F\cos\theta_1.$ Using Eqs. (8)b and (8)c, the estimates for the lateral and axial movements $\Delta d$ and $\Delta h$, see Table 1, can be easily found by using the following relations $$\Delta d = 2x(\theta_1) - s\cos\alpha_0.$$

$$\Delta h = s\sin\alpha_0 - 2y(\theta_1) \qquad (9)$$

TABLE 1

Deformation of the connecting elements

| Force F, mN | $\alpha_1$, degree | end point x, mm | end point y, mm |
|---|---|---|---|
| 0 | 30 | 0.70 | 1.21 |
| 2 | 33 | 0.74 | 1.19 |
| 10 | 50 | 0.91 | 1.06 |
| 20 | 80 | 1.14 | 0.74 |
| 30 | 111 | 1.24 | 0.36 |

The data in Table 1 were obtained with the elasticity constant, i.e. the Young's modulus of the material $E \cong 4.5 \times 10^6$ Pa; other parameters were: s=1.4 mm, a=3 mm, b=0.2 mm.

For a such lens to function the connecting component must be designed such that a force of less than 30 mN, as delivered by the ciliary muscle, results in a mutual shift of the optical elements of approximately 0.8 mm. Furthermore, for such a lens to function, the resilience of the connecting component should not exceed exerted muscle force to allow compression of the lens.

All documents referred to in the present document are considered to be incorporated in full in the present document by reference.

The invention claimed is:

1. An intraocular lens comprising at least two optical elements, each of the elements comprising:
   at least two optical surfaces, connecting and supporting components, including haptics to position the elements in the eye wherein,
   the connecting components are adapted to provide, simultaneously, lateral movement of at least one element, wherein the lateral movement is any movement perpendicular to the optical axis, and axial movement of at least one element, wherein the axial movement is any movement in the direction of the optical axis, wherein
   the connecting components comprise resilient action to revert the optical elements to a position with maximum distance between the optical elements in an absence of forces, wherein
   the connecting components include stoppers to limit the movement of the optical elements beyond a position corresponding to an emmetrope eye, wherein
   each optical element includes at least one surface adapted to provide a variable focus lens of which optical power depends on a relative lateral position of the optical element,
   each optical element includes at least one surface adapted to provide variable focus of which optical power depends on an axial position of the optical elements, and, each optical element includes at least one additional surface adapted to provide correction of at least one variable aberration other than variable focus, the aberration caused by lateral movement of the optical elements, and of which the degrees of corrections depend on the relative position of the optical elements.

2. The lens according to claim 1, wherein the lens provides a lateral movement which is a translation of at least one of the optical elements along a single axis perpendicular to the optical axis.

3. The lens according to claim 1, wherein the lens provides a lateral movement which is a rotation of at least one of the optical elements in a plane perpendicular to the optical elements.

4. The lens according to claim 2, wherein the lens provides translational movement and rotation of at least one of the optical elements.

5. The lens according to claim 1, wherein the lens further comprises at least one optical surface of a fixed optical power adapted to provide correction to a fixed refractive error of an eye due to a removal of a natural lens.

* * * * *